United States Patent [19]

Steinberg

[11] 4,197,421

[45] Apr. 8, 1980

[54] SYNTHETIC CARBONACEOUS FUELS AND FEEDSTOCKS

[75] Inventor: Meyer Steinberg, Huntington Station, N.Y.

[73] Assignee: The United States of America as represented by the United States Department of Energy, Washington, D.C.

[21] Appl. No.: 934,765

[22] Filed: Aug. 17, 1978

[51] Int. Cl.² ............................................. C07C 1/12
[52] U.S. Cl. ..................................... 585/733; 204/98; 204/101; 260/449.5
[58] Field of Search ........................ 260/676 R, 449.5; 204/101, 98; 585/733

[56] References Cited

U.S. PATENT DOCUMENTS

| 3,519,488 | 7/1970 | Gimer ................................... 204/103 |
| 3,692,649 | 9/1972 | Prigant et al. ........................ 204/101 |
| 4,076,761 | 2/1978 | Chang et al. ..................... 260/676 R |

*Primary Examiner*—C. Davis
*Attorney, Agent, or Firm*—R. V. Lupo; Leonard Belkin; Cornell D. Cornish

[57] ABSTRACT

This invention relates to the use of a three compartment electrolytic cell in the production of synthetic carbonaceous fuels and chemical feedstocks such as gasoline, methane and methanol by electrolyzing an aqueous sodium carbonate/bicarbonate solution, obtained from scrubbing atmospheric carbon dioxide with an aqueous sodium hydroxide solution, whereby the hydrogen generated at the cathode and the carbon dioxide liberated in the center compartment are combined thermocatalytically into methanol and gasoline blends. The oxygen generated at the anode is preferably vented into the atmosphere, and the regenerated sodium hydroxide produced at the cathode is reused for scrubbing the $CO_2$ from the atmosphere.

10 Claims, 1 Drawing Figure

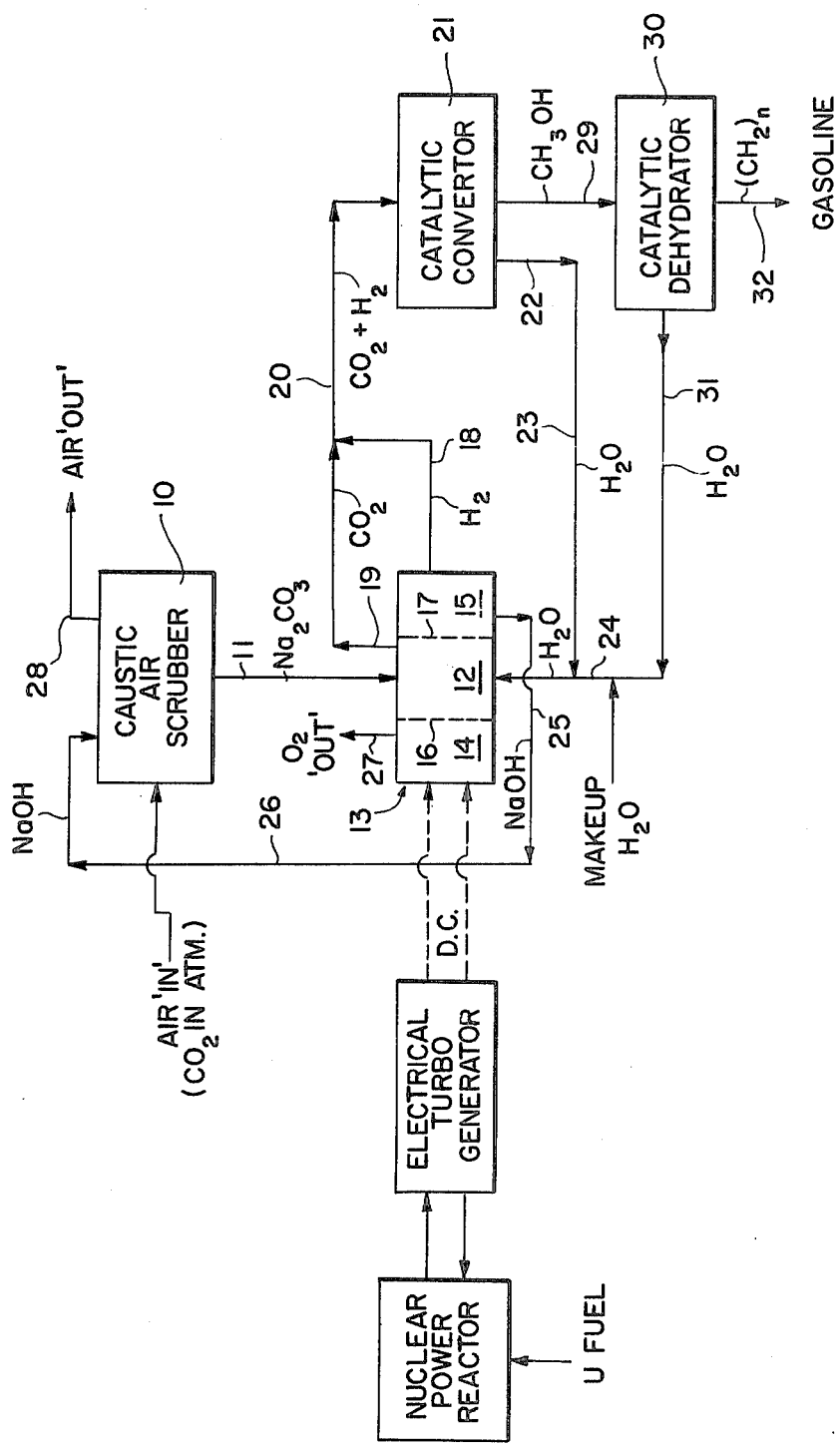

SYNTHETIC CARBONACEOUS FUELS AND FEEDSTOCKS

BACKGROUND OF THE INVENTION

This invention was made under, or during, the course of, a contract with the U.S. Department of Energy.

This invention relates to a process for producing synthetic fuels and chemical feedstocks such as gasoline, methane and methanol from gaseous $CO_2$ and $H_2$ by extracting $CO_2$ from the air with a NaOH solution; subjecting the resulting sodium carbonate solution to electrolysis in a three compartment electrolytic cell where hydrogen is formed at the cathode, oxygen at the anode and $CO_2$ is released in the center compartment; and combining the hydrogen and the $CO_2$ thermocatalytically to form gasoline.

Raw synthesis gas containing hydrogen and carbon oxide and/or carbon dioxide useful in the synthesis of methanol, methane, and gasoline are normally obtained from the conversion of coal and other hydrocarbons by a variety of known methods. The resultant synthesis gas contains impurities such as sulfur compounds, nitrogen compounds, particulate matter, etc., which require purification prior to its utilization in gasoline synthesis.

It has now been found that instant invention utilizes the atmosphere as a source of the oxides of carbon (CO and $CO_2$), from which pure $CO_2$ is recovered in a three compartment electrolytic cell together with electrolytic $H_2$ to produce synthetic fuels.

The advantages of using atmospheric $CO_2$ as a source for the synthesis gas in the synthesis of gasoline are multifold.

A vast natural resource is readily available. A desirable $CO_2$ balance between the biosphere and the atmosphere can be maintained by the removal of the $CO_2$ from the atmosphere. A pure $CO_2$ gas and $H_2$ gas is obtained from the electrolytic cell for use in the synthesis of carbonaceous fuel. The atmospheric $CO_2$ provides an alternate and extended supply of premium synthetic carbonaceous fuel for this country thus advancing the goal of energy self-sufficiency. It would eliminate many environmental and safety problems inherent in fossil fuel utilization. It is more economical.

Accordingly, it is a primary object of instant invention to provide a process for extracting $CO_2$ from the atmosphere and combining this with electrolytic hydrogen to produce synthetic gas and gasoline.

Another object of instant invention is to provide a process for extracting $CO_2$ from the atmosphere with sodium hydroxide, and electrolytically decomposing the resulting sodium carbonate solution into the concommitant generation of hydrogen and the release of concentrated $CO_2$ which are then thermocatalytically combined to form gasoline.

Still another object is to provide a three compartment sodium carbonate electrolysis cell for the concommitant production of $CO_2$ and hydrogen.

Accordingly, instant invention relates to a process of producing synthetic fuels and chemical feedstocks such as gasoline, methane and methanol from atmospheric carbon dioxide which comprises extracting atmospheric $CO_2$ from the air with an aqueous sodium hydroxide solution whereby a sodium carbonate solution is formed; electrolyzing said sodium carbonate solution in a three compartment electrolytic cell whereby hydrogen is formed at the cathode, oxygen at the anode and $CO_2$ is released in the center compartment; and thermocatalytically combining the hydrogen and carbon dioxide to form methanol which is thermocatalytically dehydrated to gasoline.

More specifically, in the process of producing synthetic fuels and chemical feedstocks such as gasoline, methane and methanol which comprises converting a gaseous mixture of hydrogen and carbon dioxide to methanol and then gasoline by thermocatalytic means; the improvement which comprises electrolyzing an aqueous sodium carbonate/bicarbonate solution in a three compartment electrolytic cell, said carbonate solution being obtained by scrubbing atmospheric carbon dioxide with an aqueous sodium hydroxide solution, whereby the hydrogen generated at the cathode and the carbon dioxide liberated in the center compartment are combined thermocatalytically into methanol and gasoline blends.

PRIOR ART

Electrolysis of electrolytic solutions in three compartment cells is generally known, as disclosed in U.S. Pat. No. 1,126,627 wherein an alkali chloride solution is electrolyzed into NaOH and HCl; U.S. Pat. No. 3,017,338 wherein a high purity alkali metal hydroxide and halogen is obtained from an alkali metal halide solution; and U.S. Pat. No. 3,135,673 wherein an acid salt such as sodium bisulfate is recovered from the anode and sodium hydroxide is recovered at the cathode when feeding a nearly saturated sodium sulfate solution into the center compartment. This patent also discloses that the sodium hydroxide catholyte is conducted to a scrubbing apparatus wherein the carbon dioxide from the atmosphere is absorbed by said caustic, forming a sodium carbonate solution which is combined with an equivalent amount of the anolyte effluent sodium bisulfate to regenerate the original sodium sulfate which can be recycled to the electrolytic cell.

The removal of $CO_2$ from gas streams, such as the atmosphere, by intimate contact with, and absorption into a solution of a strong base such as sodium hydroxide whereby sodium carbonate is formed, and the regeneration of said spent absorbent in a two compartment electrolytic cell, using said sodium carbonate as an electrolyte, is also well known in the prior art, as disclosed in U.S. Pat. Nos. 3,519,488 and 3,692,649. However, both of aforesaid patents require the presence of substantial amounts of a salt in addition to the alkali metal hydroxide in the scrubbing solution. For example, U.S. Pat. No. 3,519,488 uses solutions of potassium hydroxide and potassium carbonate and U.S. Pat. No. 3,692,649 uses inert salts such as $NaClO_4$, $KCH_3CO_2$, $NaCH_3CO_2$, NaCl, KCl, $Na_2SO_4$ and $K_2SO_4$, together with the alkali metal hydroxide base. U.S. Pat. No. 3,519,488 further adds a neutral electrolyte such as KF or $K_2SO_4$ to the anolyte soltion to overcome problems encountered in the electrolysis of the spent scrubbing solution containing the alkali metal carbonate.

Other patents which disclose a two compartment electrolytic cell containing an alkali metal carbonate electrolyte useful in the collection and concentration of carbon dioxide are U.S. Pat. Nos. 3,401,100 and 3,494,842.

Although the prior art discloses a three compartment electrolytic cell generally, and U.S. Pat. No. 3,135,673 discloses a three compartment cell containing sodium carbonate as the partial electrolyte together with the bisulfate, the recovery of $CO_2$ in the center compartment for combination with the hydrogen released at the cathode as in instant invention is not disclosed. These patents only disclose the formation of an acid anolyte and a basic catholyte with unreacted salt in the center compartment.

Similarly, although the prior art discloses the extraction of $CO_2$ from the atmosphere with a sodium hydroxide solution whereby sodium carbonate is formed, and the regeneration of the sodium hydroxide in an electrochemical cell, the simultaneous liberation of $CO_2$ and hydrogen as in instant invention is not disclosed.

Furthermore, there is no recognition in the prior art that $CO_2$ from the atmosphere can be utilized in the formation of a sodium carbonate electrolyte for a three compartment electrolytic cell capable of producing a substantially pure synthesis gas for the production of synthetic fuel. The use of conventional synthesis gas obtained from coal, shale oil and other carbonaceous feedstocks containing hydrogen and carbon dioxide in the production of methanol and gasoline is well known in the art as disclosed by U.S. Pat. Nos. 3,950,369; 4,065,483; and 4,076,761. However, aforesaid synthesis gases are impure, and require purification steps which are costly and time-consuming.

DESCRIPTION OF THE INVENTION

The process, according to this invention, depends on the electrolytic decomposition of water containing higher concentrations of carbonate/bicarbonate ion, which is essentially the electrolytic decomposition of sodium carbonate/bicarbonate thus forming caustic, $H_2$, $O_2$ and $CO_2$.

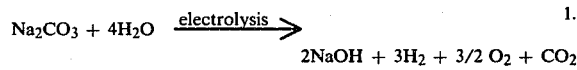

1.

It has been found that water can be electrolytically decomposed to $H_2$ and $O_2$ in a sodium carbonate/bicarbonate cell releasing $CO_2$ in addition to $O_2$ at the anode and $H_2$ at the cathode. The theoretical cell voltage is approximately 3.0 volts per mole. of $H_2$. This compares to 2.4 volts for the decomposition of water. However, if a three compartment cell is used, the $CO_2$ can be separated in a center compartment. Referring to the flow sheet in the FIGURE, the regenerated caustic is then used to scrub the $CO_2$ from the atmosphere and the $CO_2$ recovered from the cell is combined with hydrogen catalytically to form methanol and gasoline blends. In this case, the oxygen is vented to the atmosphere. It may also be possible to operate the carbonate cells under pressure to match the operating conditions of the catalytic convertors so as to eliminate compression. The cell may be operated at elevated temperature (100°-150° C.) to improve efficiency when under pressure. The system, however, is essentially an isothermal one for removal and recovery of $CO_2$ compared to the absorption-stripping process utilizing dilute potassium carbonate which is slow to absorb atmospheric $CO_2$ and requires stripping by means of heat exchange and distilling at high temperature. Furthermore, no additional cell equipment, power requirement and corrosion problems are encountered as existed in the use of electrolytic sodium chloride cells which produced caustic for $CO_2$ scrubbing and the chlorine for neutralizing the sodium carbonate formed. The use in instant invention, of a sodium carbonate electrolytic cell eliminates the disadvantages of both aforesaid processes, thereby reducing capital and operating costs.

This electrolytic carbonate system may also be used for stack gas scrubbing of $CO_2$. However, in this case where $CO_2$ gas compositions up to 15% are available compared to 0.035% in the atmosphere, adoption of a conventional absorption/stripping technique may be more economical.

The FIGURE shows by way of example a flow sheet of the process according to this invention with a diagrammatic representation of the three compartment electrolytic cell.

A gas stream containing atmospheric $CO_2$ is fed to a caustic air scrubber 10 containing an aqueous NaOH solution containing about 5 to 25% NaOH and at ambient temperatures of about 10°-25° C., wherein $Na_2CO_3$ is formed in accordance with the following reaction:

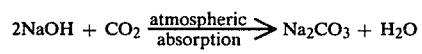

2.

The resulting sodium carbonate solution is conveyed via line 11 to the center compartment 12 of a three compartment electrolytic cell 13 provided with an anode compartment 14 and a cathode compartment 15, and a suitable anode and cathode respectively (not shown), said anode compartment 14 being separated from the center compartment 12 by means of a hydraulically permeable non-permselective diaphragm 16 or an anion-permselective membrane 16, and said cathode compartment 15 being separated from said center compartment 12 by means of a cation-permselective membrane 17. About 50% of the $Na_2CO_3$ exists in the form of $NaHCO_3$ in the electrolytic cell as shown by the following equation:

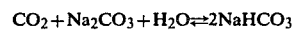

The construction of electrolytic cell 13 is known in the art as described in U.S. Pat. No. 3,135,673 which is incorporated herein by reference. The electrolytic cell is operated at 3 to 3.5 volts and a current of 200 to 700 amp/sq.ft. and at a temperature below the boiling point of the electrolyte, such as about 25°-60° C. However, when this cell is operated under pressure to coincide with the operating conditions of the catalytic convertors so as to eliminate compression, temperatures of about 100°-150° C. are utilized. Although the diagram illustrates a single electrolytic cell, it is understood that a multiple cell structure is utilized, wherein the cells are connected in series. Pure gaseous hydrogen is removed from the cathode compartment 15 via exit pipe 18 and pure $CO_2$ gas is released from center compartment 12 via exit pipe 19, and both are fed directly via line 20 to a catalytic convertor 21 of any conventional design and containing a copper catalyst or other suitable catalyst, wherein methanol and water are formed in accordance with the following reaction:

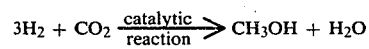

3.

The water is removed from said convertor 21 via exit line 22 and recycled via lines 23 and 24 into electrolytic cell 13. It is preferable to recycle the water to line 11 and mix directly with the carbonate electrolyte prior to its introduction into electrolytic cell 13. Sodium hydroxide is removed from cathode compartment 15 via exit line 25 which is recycled via line 26 into the caustic air scrubber 10 for reuse. Some non-critical amounts of sodium carbonate may remain mixed with the recycled sodium hydroxide without affecting the function of the subject invention. Oxygen gas is vented into the atmosphere from anode compartment 14 via exit 27. The air depleted of its $CO_2$ content is vented from air scrubber 10 via outlet line 28.

The methanol formed in convertor 21 is conveyed via line 29 to a catalytic dehydrator 30 of conventional design and containing a zeolite catalyst, to produce gasoline and water in accordance with the following reaction:

$$n CH_3OH \xrightarrow{\text{catalytic dehydration}} (CH_2)_n + nH_2O \quad 4.$$

The water is withdrawn via line 31 and is also recycled and fed into electrolytic cell 13, preferably by first mixing directly with the carbonate electrolyte, and the gasoline fraction is withdrawn via exit 32. Reactions 3 and 4 are exothermic and do not require any energy input.

The electrolytic carbonate cell 13 may be powered by any electrical source of D. C. power. However, the most economical source of power is a nuclear power reactor which powers an electrical turbo generator which supplies the direct current needed for the electrolysis of the sodium carbonate/bicarbonate cell.

The three compartment sodium carbonate/bicarbonate electrolytic cell operates at about 3 to 3.5 volts and at a current density of about 200 to 700 amp/sq.ft. to effect decomposition of the carbonate solution into 3 moles hydrogen, 3/2 moles oxygen, 1 mole carbon dioxide and 2 moles sodium hydroxide, in accordance with reaction 1. The molar ratio of 3:1 of the hydrogen gas to the carbon dioxide gas released in this electrolysis reaction coincides with the molar ratio needed for the catalytic reaction to produce methanol as shown in reaction 3. If it is desired to produce methane in lieu of methanol, the molar ratio of the reactants hydrogen to carbon dioxide is 4:1, requiring the addition of one mole hydrogen to the catalytic convertor.

This process is applicable to atmospheric gas streams containing dilute amounts of $CO_2$ such as 0.035% by volume of $CO_2$ normally found in the atmosphere and up to a maximum of 20% by volume of $CO_2$ found in stack gas emissions from the burning of fossil fuel.

The following example is merely illustrative of present invention and is not to be construed as limited thereto.

EXAMPLE

A 10% caustic solution containing about 2.5 lbs of NaOH is used to counter-currently scrub the carbon dioxide from the atmosphere in a packed column at ambient temperatures (about 25° C.). About 43,000 cu ft of air is used. In this manner 1.38 lb of $CO_2$ is scrubbed from the atmosphere which has a concentration of 350 parts per million by volume. About 80% of the $CO_2$ is recovered from the air. The resulting sodium carbonate/bicarbonate solution is sent to a 3 compartment electrolysis cell at a temperature below boiling such as about 25°–60° C., where a D. C. electric current of 3 to 3.5 volts and a current of 200–700 amp/sq.ft. decomposes the carbonate solution. In the cathode compartment $H_2$ is released and 0.19 lbs of $H_2$ is collected. At the anode 1.52 lbs oxygen is released and vented to the atmosphere. In the center compartment the 1.38 lbs of $CO_2$ is released. The purified recovered $H_2$ and the $CO_2$ are collected, compressed to between 50 and 100 atm, and heated to 350° C. over a copper catalyst where 1 lb of methanol is produced. The methanol can be further dehydrated over a zeolite catalyst at 350° C. and 100 atm to a gasoline distillate weighing 0.45 lbs. The latter two processes are well known in the art.

Instant novel process of converting $CO_2$ from the atmosphere to synthetic methanol and synthetic carbonaceous fuels with electrolytically generated hydrogen and oxygen in a three compartment carbonate electrolytic cell is a continuous, cyclic, efficient and economical process. The use of air and water as the starting materials eliminates impurities, and the use of a carbonate electrolytic cell in lieu of the prior art bisulfate cell or sodium chloride cell eliminates corrosion problems and contaminants which would poison the copper catalyst component used in the methanol synthesis. Since the removal and recovery of $CO_2$ in a carbonate electrolytic cell is an isothermal process, no heating is necessary and there is no pressure drop nor a large loss in heat exchange. This system is also adaptable to the production of methane by merely adding one additional mole of hydrogen to the catalytic convertor. The recycling of the sodium hydroxide and the water for reuse in this process eliminates waste and renders this process particularly desirable for economic and efficiency reasons.

The applications of this process can be very broad. For example, this process can be used in the production of synthetic fuels at sea aboard nuclear aircraft carriers using nuclear power, air and sea water. This jet fuel can be utilized by aircraft.

I claim:

1. In the process of producing synthetic fuels and chemical feedstocks such as gasoline, methane and methanol by converting a gaseous mixture of hydrogen and carbon dioxide to methanol and then gasoline by thermocatalytic means; the improvement which comprises extracting atmospheric carbon dioxide with an aqueous sodium hydroxide solution to form a carbonate solution, electrolyzing said aqueous sodium carbonate/bicarbonate solution in a three compartment electrolytic cell to generate pure hydrogen at the cathode and pure carbon dioxide in the center compartment, and combining said pure hydrogen gas with said pure carbon dioxide gas thermocatalytically to form methanol and gasoline blends.

2. A process according to claim 1, wherein oxygen generated at the anode is vented into the atmosphere.

3. A process according to claim 1, wherein the sodium hydroxide is regenerated at the cathode.

4. A process according to claim 3, wherein the regenerated sodium hydroxide is recycled to scrub carbon dioxide from the atmosphere.

5. A process according to claim 1, wherein the water of reaction resulting from the catalytic conversion of the gaseous mixture of hydrogen and carbon dioxide into methanol and then gasoline, is recycled to the three compartment electrolytic cell.

6. A process according to claim 1, wherein the three compartment electrolytic cell operates at about 3 to 3.5 volts and a current density of about 200 to 700 amps/sq.ft.

7. A process in accordance with claim 1, wherein the atmospheric gas stream may contain 0.035% to 20% by volume of carbon dioxide.

8. A process in accordance with claim 1, which is a continuous process.

9. A process in accordance with claim 1, wherein the aqueous sodium hydroxide solution contains about 5-25% sodium hydroxide.

10. A process in accordance with claim 1, wherein the electrolytic cell is operated below the boiling point of the electrolyte.

* * * * *